United States Patent
Sorensen et al.

(10) Patent No.: US 10,576,473 B2
(45) Date of Patent: Mar. 3, 2020

(54) METHOD AND DEVICE FOR PREVENTION OF SPLASHING OF NON-CAPPED FLUID SAMPLE DURING TRANSPORT ON DIAGNOSTIC LABORATORY EQUIPMENT

(71) Applicant: Siemens Healthcare Diagnostics Inc., Tarrytown, NY (US)

(72) Inventors: Keld Sorensen, Tucson, AZ (US); Baris Yagci, Montclair, NJ (US); Robert Hempton, Wayne, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 149 days.

(21) Appl. No.: 15/751,382

(22) PCT Filed: Aug. 25, 2016

(86) PCT No.: PCT/US2016/048556
§ 371 (c)(1),
(2) Date: Feb. 8, 2018

(87) PCT Pub. No.: WO2017/040171
PCT Pub. Date: Mar. 9, 2017

(65) Prior Publication Data
US 2018/0257071 A1 Sep. 13, 2018

Related U.S. Application Data (60) Provisional application No. 62/212,452, filed on Aug. 31, 2015.

(51) Int. Cl.
*B01L 3/00* (2006.01)
*G01N 1/14* (2006.01)

(52) U.S. Cl.
CPC ....... *B01L 3/50825* (2013.01); *B01L 3/50215* (2013.01); *B01L 2200/06* (2013.01); *B01L 2200/14* (2013.01); *G01N 2001/1418* (2013.01)

(58) Field of Classification Search
CPC ............ B01L 3/50215; B01L 3/50825; B01L 3/502746; G01N 2035/00287
See application file for complete search history.

(56) References Cited

U.S. PATENT DOCUMENTS 3,972,812 A * 8/1976 Gresl, Jr. ............. B01D 33/015
                                                        210/782
4,150,089 A    4/1979 Linet
(Continued)

FOREIGN PATENT DOCUMENTS

CN     201222009 Y    4/2009
JP     H01 111656     4/1989
(Continued)

OTHER PUBLICATIONS

Extended EP Search Report dated Apr. 18, 2019 of corresponding European Application No. 16842629.4, 5 Pages.
(Continued)

*Primary Examiner* — Justin N Olamit (57) ABSTRACT

An assembly for mitigating spillage of patient sample in a patient sample tube having an open top includes a patient sample in the tube and a layer of inert material floating on the sample fluid, such that the material restricts splashing movement of the sample's surface. The material can include a foam, a gel, or a disk. The disk can be approximately the diameter of the sample tube with a center opening configured to accept a pipette to provide access to the patient sample.

13 Claims, 4 Drawing Sheets

(56) References Cited

U.S. PATENT DOCUMENTS

| | | | |
|---|---|---|---|
| 5,091,304 A * | 2/1992 | La Duca | G01N 33/86 |
| | | | 435/13 |
| 5,393,674 A * | 2/1995 | Levine | B01L 3/50215 |
| | | | 436/177 |
| 5,403,388 A | 4/1995 | Pfiffner et al. | |
| 5,411,876 A | 5/1995 | Bloch et al. | |
| 5,632,905 A * | 5/1997 | Haynes | B01L 3/50215 |
| | | | 210/782 |
| 7,726,180 B2 * | 6/2010 | Kanahara | B01L 3/00 |
| | | | 114/267 |
| 2009/0139326 A1 | 6/2009 | Kanahara | |
| 2013/0116102 A1 | 5/2013 | Hansen | |

FOREIGN PATENT DOCUMENTS

| | | |
|---|---|---|
| JP | 2005 083777 A | 3/2005 |
| WO | 96/25712 A1 | 8/1996 |
| WO | 2006/007455 A1 | 1/2006 |

OTHER PUBLICATIONS

PCT International Search Report and Written Opinion dated Nov. 4, 2016 (10Pages).

\* cited by examiner

METHOD AND DEVICE FOR PREVENTION OF SPLASHING OF NON-CAPPED FLUID SAMPLE DURING TRANSPORT ON DIAGNOSTIC LABORATORY EQUIPMENT

CROSS-REFERENCE TO RELATED APPLICATIONS

This application claims priority to U.S. provisional application Ser. No. 62/212,452 filed Aug. 31, 2015, which is incorporated herein by reference in its entirety.

TECHNOLOGY FIELD

The present invention relates, generally, to sample handling in an in vitro diagnostics environment, and more particularly, to materials to be added to fluid samples in an IVD environment. Embodiments of the present invention are particularly well suited, but in no way limited, to providing an improved method for facilitating movement of fluid samples in an automation system or sample handling system to minimize or reduce risk of splashing fluid samples.

BACKGROUND

Various types of analytical tests related to patient diagnosis and therapy can be performed by analysis of a liquid sample taken from a patient's bodily fluids, or abscesses. These assays are typically conducted with automated clinical analyzers onto which tubes or vials containing patient samples have been loaded. The analyzer extracts a liquid sample from the vial and combines the sample with various reagents in special reaction cuvettes or tubes (referred to generally as reaction vessels). Usually the sample-reagent solution is incubated or otherwise processed before being analyzed. Analytical measurements are often performed using a beam of interrogating radiation interacting with the sample-reagent combination, for example, turbidimetric, fluorometric, absorption readings, or the like. The measurements allow determination of end-point or rate values from which an amount of analyte related to the health of the patient may be determined using well-known calibration techniques.

Clinical chemistry analyzers typically include a plurality of stations or modules that interact with patient samples. Each module can be specialized to a type of test, calibration, or sample handling task. Commonly, an automation system is employed to shuttle samples from one module to another, allowing each module to perform tasks on the patient sample in an automated fashion. Traditionally, such automation systems have included slow speed friction tracks (<1 m/sec) that slowly move patient samples from one point to another point in the automation system. This can result in long latency and low throughput. For example, if an analyzer is 50 meters from the sample entry point, and the track is operating at a speed of 0.2 m/sec, it will take 250 seconds (over 4 minutes) from the sample entry until it is received by the analyzer. This transport time adds to the overall turn-around time (TAT) of samples analyzed by the system and is undesired.

It is desirable for patient samples to move through the automation system as quickly as possible to reduce overall system latency. An example of an automation system that can be used to reduce the transit time of patient samples in an automation system can be found in commonly owned U.S. patent application Ser. No. 14/376,107, incorporated herein by its entirety.

While it is desirable to minimize transit times on an automation track, traditionally speeds were limited intentionally to minimize acceleration and jerk forces applied to patient samples. Typically, patient samples are transported in patient sample tubes, such as test tubes. Because capping and uncapping a sample tube is a precise mechanical operation, capping and uncapping operations are typically handled by hand or by the use of a dedicated capper/decapper station that has been developed to precisely remove and align and apply caps to patient sample tubes. As result, sample tubes are typically de-capped, placed into the automation system, shuttled between various modules, portions of that sample are aspirated at each module, and the sample tube is returned for recapping by hand or at a dedicated capping station. Thus, patient samples are often moved via the automation system in an uncapped state.

Because of the biohazardous and sensitive nature of patient samples, it is desirable, and often a requirement, that the automation system does not cause spilling of the patient sample, which could contaminate the automation track or other samples. The traditional way this was accomplished has been by reducing the overall speed of the automation system, so as to minimize forces on the patient sample tube. This prevents splashing, spilling, and frothing, but reduces the overall speed of the automation system, increasing latency.

SUMMARY

Embodiments of the present invention address and overcome the above shortcomings and drawbacks by applying a layer or material that floats on top of the sample fluid. This material helps to dampen or arrest waves from forming that can result in splashing.

Some embodiments of the present invention are directed to an assembly used in clinical analysis that includes a patient sample tube having an open mouth at one end and patient sample fluid contained within the sample tube. A layer of material floats on a top surface of the patient sample fluid, such that the layer of material floats and restricts splashing movement of the top surface.

According to one aspect of the invention, the material is foam, gel, or non-porous material. According to another aspect of the invention, the material is a floating disk having an opening at the center substantially larger than a pipette diameter. The opening can be substantially circular or include radial channels.

Some embodiments of the present invention are directed to method for mitigating spillage of a patient sample in a laboratory automation system including steps of de-capping a patient sample tube (a glass or plastic tube having an opening and a patient sample fluid contained therein), placing a layer of material floating on a top surface of the patient sample fluid such that the layer of material floats and restricts splashing movement of the top surface, transporting the patient sample to a pipette station, inserting a pipette through the layer of material, and aspirating a portion of the patient sample fluid via the pipette.

Some embodiments of the present invention are directed to an apparatus configured to mitigate spillage of patient sample tubes that includes a patient sample tube comprising a cylindrical material having a closed end configured to hold a patient sample fluid and an open end configured to accept a pipette, and a round, substantially flat disk configured to be placed within a patient sample tube and to float on the patient sample fluid, comprising a center opening configured to accept the pipette and provide access to the patient sample fluid without exposing the entire surface of the patient sample fluid.

According to one aspect of the invention, the center opening is substantially circular or includes radial channels. According to another aspect of the invention, the disk is constructed of one of polypropylene and polystyrene. According to another aspect of the invention the disk has a hollow structure such that the average density is less than the density of the patient sample fluid.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION OF ILLUSTRATIVE EMBODIMENTS

The above problems in the prior art have motivated the discovery of improved apparatus and methods for reliably and/or automatically facilitating movement of patient samples in an uncapped state throughout an automation system, with a reduced emphasis on minimizing lateral and tangential forces on the patient sample. By providing a system that reduces the risk of splashing or spilling, samples may be transported via an automation track at higher rates of speed, with less concern about the amount of force applied to that sample. This can greatly reduce latency, improving turnaround times (TAT) and overall throughput of the automation system.

Ordinarily, fast speeds in an automation system can result in vigorous movement of test tubes containing patient samples. In an uncapped state, patient samples exposed to vigorous movement can be made to slosh, splash, froth, or spill. Thus, while it is desirable to keep these samples uncovered to reduce the need for de-capping at each station the automation system, each time a portion of the sample should be aspirated, vigorous movement should be avoided for uncapped samples.

Embodiments of the present invention facilitate fast automation speeds (and potentially vigorous movement) while allowing the patient sample tube to travel in uncapped state along the automation track. This is generally accomplished by providing a physical impediment to the splashing of the patient sample. Splashing is typically caused by rapid movement of the surface of a patient sample due to lateral or transverse forces in the horizontal direction. This can be due to acceleration or jerk when changing the velocity of a patient sample during acceleration or deceleration on a straightaway or along a turn in the automation track. By providing an impediment to large amounts of motion in the surface of the patient sample, splashing and therefore spilling can be reduced.

A traditional cap on a sample tube provides a physical barrier at the top of the patient sample tube. This top is typically well above the surface of a patient sample. Thus, the patient sample inside of the capped tube can splash and slosh because the surface of the patient sample is unhindered. However, the sample does not spill because any splashing liquid that reaches the top of the tube cannot penetrate the cap. Any splashed sample that reaches the top of the tube can partially adhere to the underside of the cap or spill back into the sample tube.

In embodiments, placing a material or object (i.e., a material layer) that floats on the surface of the patient sample mitigates spillage of a de-capped sample. In doing so, the previously unrestricted movement of the surface of the patient sample during acceleration can be restricted. In some embodiments, a foam that has an average density of less than the average density of the patient sample can be placed atop the patient sample, allowing the foam to float. By choosing a foam that has substantial viscosity, the viscosity of the foam can act to dampen sudden oscillations in the surface of the patient sample that lead to splashing. This can allow a movement in the patient sample to be less violent, greatly reducing the risk that a portion of the patient sample will be ejected from the sample tube.

In some embodiments, a gel that has an average density of less than the average density of the patient sample can be placed atop the patient sample. Like the foam embodiment, a viscosity or mechanical modulus (e.g., shear modulus) of the gel can dampen or restrict violent oscillations and serve as the patient sample.

In some embodiments, a disk made from a material of an average density less than the average density of the patient sample can be placed on the surface of the patient sample, allowing the disk to float and provide surface integrity that restricts the motion of the surface of the patient sample. A floating disk can act like a loose cap that rides atop the surface of the fluid, moving with the surface, but restricting rapid motion on that surface, dampening the motion on the surface that causes splashing. An opening in the center of the disk allows a pipette to enter the fluid without substantial interference from the disk.

Each of these embodiments provides some degree of physical barrier that must be overcome to eject a portion of the patient sample out of the tube to spill the patient sample during manual movement or during an automation process. This allows the patient sample tube to undergo a higher degree of acceleration or vigorous movement during transit than an unrestricted patient sample. This can allow automation mechanisms to move faster than traditional automation systems. This can also help prevent spilling at higher risk portions of the automation system, such as curves or other transitions, such as stopping and starting points. As a result, lab automation systems using embodiments of the present invention may be capable of higher throughput, increased travel speeds, or a larger number of samples to be handled on any given track portion of the automation system. This can reduce the overall latency/TAT of patient samples.

Figure 1:
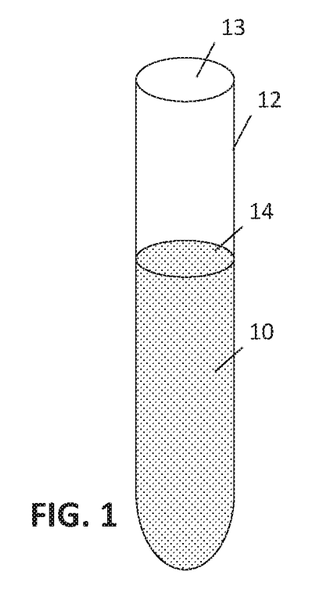
FIG. 1 is a perspective view of an uncapped patient sample tube.

FIG. 1 shows an uncapped sample tube for use with embodiments and with traditional automation systems. A sample fluid 10 is contained in a sample tube 12 having a top opening 13. The top surface 14 of the fluid sample is exposed in FIG. 1, which makes sample 10 prone to splashing under sudden acceleration. Sample tube 12 is generally a glass or transparent plastic tube having a rounded, closed end at the bottom to hold the patient sample fluid, an open end at the top that is configured to receive a cap (e.g., a friction fit cap) and to accept a pipette when uncapped, and cylindrical walls that are substantially parallel between the two ends. Typically tubes are moved throughout the laboratory environment via trays holding a large number of tubes (e.g., 55) that can be carried or accepted by an automation system or via carriers that hold a small number of tubes (generally one, but carriers can be configured to hold a handful of tubes) that are designed to traverse an automation system.

Figure 2:
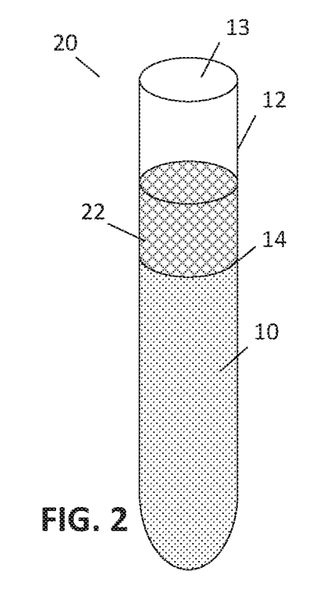
FIG. 2 is a perspective view of an uncapped patient sample tube with a foam floating on top of the patient sample fluid.

FIG. 2 shows a configuration 20 whereby a foam 22 is applied to surface 14. Foam 22 can be applied via any conventional means, such as a pressurized foam or a two-part foam that is combined and dispensed via a nozzle tip that can be inserted into opening 13 of sample tube 12. Foam can be dispensed anywhere between opening 13 and surface 14. Because the density of foam 22 is less than that of sample fluid 10, the foam will form and float on top of the fluid. The density of the foam can be manipulated to control the density or size of air/gas bubbles to result in a density that allows the foam to float on surface 14. Exemplary materials for the foam can include any suitable foam known in the art that will not react with the patient sample, will not leave a residue on the pipette that will be inserted through the foam to access the patient sample, will not clog the pipette, and ideally the material is not electrolytic or conductive, which can prevent interference with the level sense mechanism on the pipette. In some embodiments, the level sense of a pipette can be calibrated to account for unknown approximate thickness of foam 22, if foam 22 affects the level sense signal detected by the pipette (e.g., capacitive level sense voltage). Suitable foam materials may include, any inert, hydrophobic material that readily forms a matrix with gas to form a foam. This allows the foam to float without interfering with the operations of the pipette.

Figure 3:
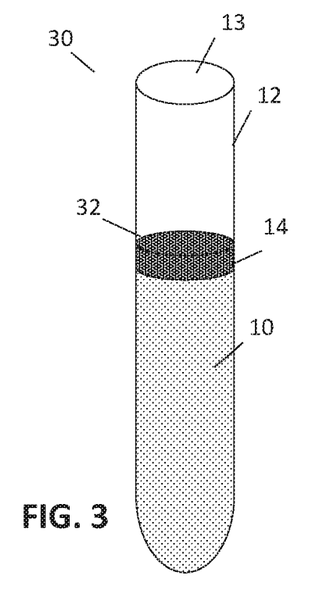
FIG. 3 is a perspective view of an uncapped patient sample tube with a gel floating on top of the patient sample fluid.

FIG. 3 shows a configuration 30 whereby a gel 32 is applied to surface 14. Gel 32 can be applied via any conventional means, such as a nozzle tip that can be inserted into opening 13 a sample tube 12 to dispense a viscous liquid gel. In some embodiments, this gel may set to some degree after dispensing, or remain in substantially the same viscous liquid state as it was when dispensed. The density of gel 32 should be less than that of sample fluid 10, allowing it to float on top of surface 14. Because the gel 32 is highly viscous and cohesive, it can provide a mechanical barrier to rapid changes in surface 14, such as would be common with sloshing, which could lead to spilling. Like foam 22, gel 32 can be any suitable gel known in the art that will not react with the patient sample, will not leave a residue on the pipette that will be inserted through the foam to access the patient sample, will not clog the pipette, and ideally the material is not electrolytic or conductive, to prevent interference with the level sense mechanism on the pipette. In some embodiments, the level sense of a pipette can be calibrated to account for unknown approximate thickness of gel 32, if gel 32 affects the level sense signal detected by the pipette (e.g., capacitive level sense voltage). In some embodiments, because the gel 32 will not be later removed from tube 12, it may be desirable to use a gel material that has some level of adhesion with the glass of sample tube 12, providing additional shear resistance to sloshing. Suitable foam materials may include any inert hydrophobic polymer material that is ideally nonconductive. Furthermore, it may be desirable for a highly cohesive gel to be used, such that the gel will separate, allowing the pipette to be inserted, without allowing a substantial amount of the gel to be aspirated as part of the sample aliquot. In some embodiments, the foam can be placed in a uniform thickness, such that the level sense mechanism can compensate for the thickness of the gel.

FIGS. 4A through 4D shows configurations and in which a disk is used to mitigate sloshing and spillage, rather than (or in some embodiments, in addition to) foam or gel floating on top of the patient sample. Each of the disks shown in FIGS. 4A-4D is a substantially flat disk configured to be placed within a patient sample tube and to float on the patient sample fluid (i.e., the average density of the disk is less than that of the fluid). Each disk has a center opening configured to accept a pipette and provide access to the patient sample fluid without exposing the entire surface of the patient sample fluid. Substantially more than half of the surface area of the sample is covered by the layer of material of the disk. For example, the radius of the opening is generally about half the radius of the disk or less. This allows access while covering most of the surface to provide substantial splash resistance. Moreover any gap between the disk and the tube walls is substantially less than the radius of the opening.

Figure 4A:
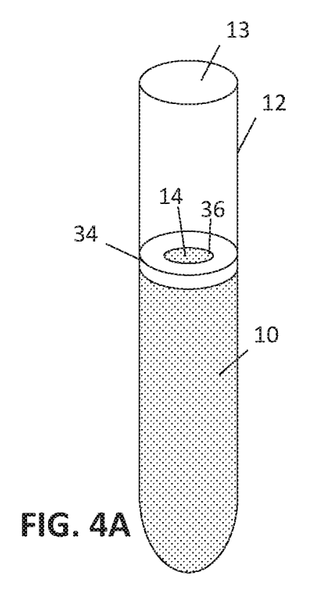
FIGS. 4A-4D are perspective views of an uncapped patient sample tube with a disk floating on top of the patient sample fluid.
Figure 4B:
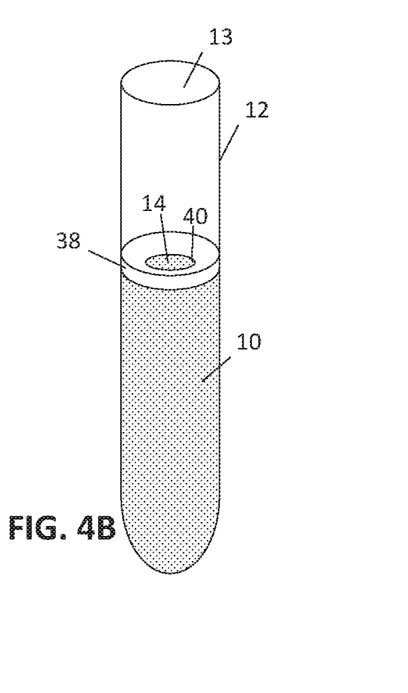
Figures 4C, 4D:
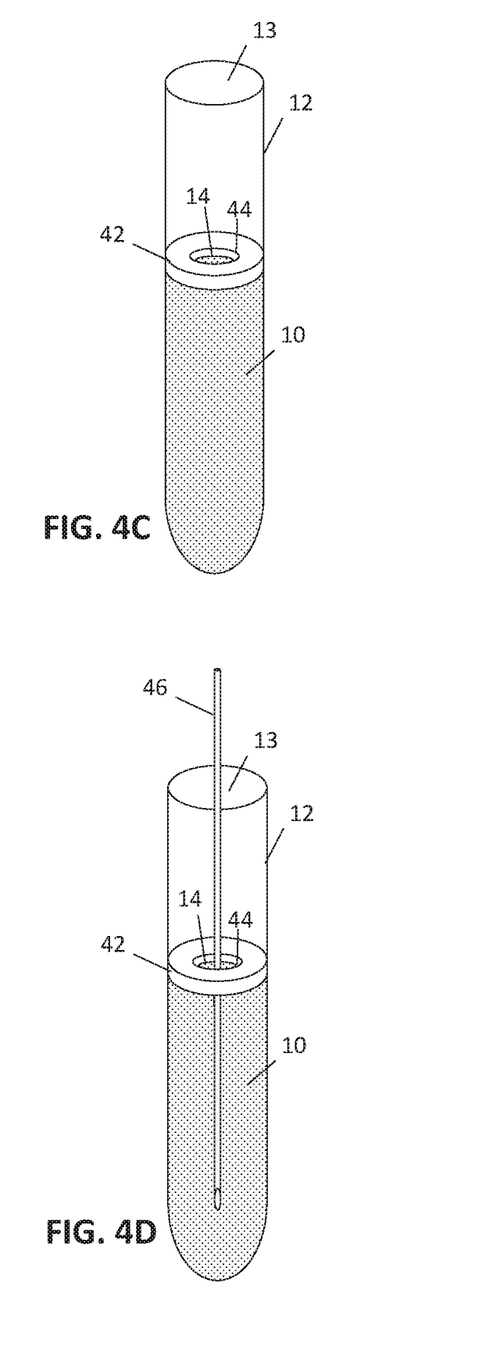
Figure 5:
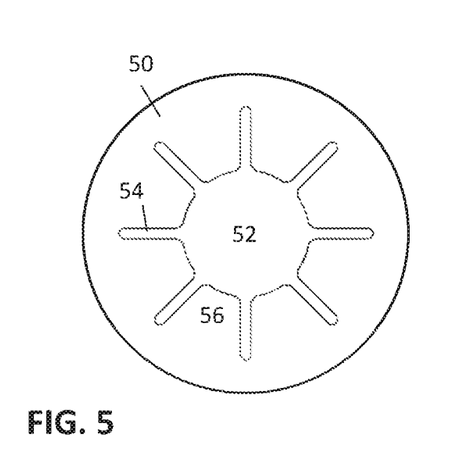
FIG. 5 is a top view of an embodiment of the disk for floating on top of the patient sample fluid.

FIGS. 4A-4C show three different cross-section approaches to the disk. In each of these embodiments, the disk is constructed of a material having sufficient average density such that the disk floats on the surface of the patient sample. In these embodiments, the disk includes an orifice that allows a pipette to enter the sample fluid in the center of the disk. The diameter and shape of the orifice can vary depending on the tolerances of positioning the pipette with respect to the center of the patient sample tube. For example, in some embodiments, the orifice can be approximately 5 mm in diameter to allow a 1 mm pipette to enter the patient sample if the center of the disk is within 2 mm of its expected location. It is desirable to have the diameter of the orifice be substantially larger (e.g., approximately twice the diameter of the pipette or much larger) than the diameter of the pipette to allow for tolerance and positioning deviation. The exact size and shape of the orifice can be selected for the tolerances of each system in which the disk is used. For example, where the diameter of the patient sample tube varies, different size disks can be used for each type of sample tube, or a common sized disk can be used with a sufficiently large orifice to accommodate shifting of the disk relative to the walls of the patient sample tube. FIG. 5 shows an embodiment where the orifice of the disk is not entirely circular, including additional radial features that extend the length of the edge of the orifice, which may improve mitigation of rapid motion of the surface of the patient sample. For simplicity, the orifices in FIGS. 4A-4D are circular, but it should be appreciated that different suitable shapes (e.g. symmetric shapes with a large central opening, such as star shapes, hexagons, octagons, or other polygons)

could be used. Although the embodiments shown in FIGS. 4A-4D do not all have perfectly rectangular cross-sections, these can all be said to be substantially flat as the top or bottom surface only deviates from horizontal less than the thickness of the disk.

Because the disks float atop the surface of the patient sample tube, different cross-sectional profiles can be used to affect how the top of the disk floats relative to the surface of the patient sample. This may be needed where optical means are used to determine the fluid height in the patient sample tube, or where it is desired that the meniscus is low relative to the top surface of the disk or at or near the top surface of the disk. As shown in FIG. 4A, the available portion of a fluid sample surface 14 is limited to the size of orifice 36 (not drawn to scale) disk 34 floats atop fluid sample 10 due to the average density of disk 34. It is generally desirable to use a nonporous material for the disk. In some embodiments, disk 34 is of uniform density, such as a low-density polyethylene or semi rigid closed cell foam material is sufficiently dense to allow it to float on the patient sample. In some embodiments, disk 34 is a nonuniform density, such as a gas-filled, hollow material or a foam filled structure. For example, a disk may be a hollow polypropylene structure filled with air or nitrogen to add buoyancy. This allows higher density materials to be used.

Disk 34 is constructed so that fluid surface 14 is substantially at or near the top surface of disk 34. This can allow optical determination of the level of the patient sample in the tube by observing the location of the disk.

FIG. 4B shows an alternative embodiment of the disk 38 having a wedge-shaped profile that allows the top surface of disk 38 to be slightly concave, such that the top surface at the edge of orifice 40 is substantially at the same height, within a fraction of a millimeter, as the top surface of the sample 14. This can mitigate mechanical action of waves in surface 14 from impacting vertical surfaces of disk 38.

In the embodiment shown in FIG. 4C, disk 42 is of substantially uniform thickness, giving disk 42 a traditional washer shape. Because disk 42 is sufficiently dense that it floats on top of surface 14, the top surface of disk 42 can be substantially above surface 14, where the height differential is determined by the density of material used for disk 42, and therefore the displacement. This creates a vertical wall at the edge of orifice 44 with respect to surface 14 of the patient sample. Depending on the hygroscopic nature of the material used for disk 42, this sidewall can create a meniscus with surface 14, allowing additional adhesion of disk 42 to the patient sample to further mitigate sloshing.

In the embodiment shown in FIG. 4D, a pipette 46 is inserted into orifice 44, approximately at the center of the orifice 44. It should be noted, the exact location of pipette 46 with respect to orifice 44 depends on a shifting of disk 42 with respect to tube 12, such as when the diameter of the disk is substantially less than the inner diameter of tube 12, as well as any positioning error of the tube relative to the pipette. This differential can be due to manufacturing tolerances or designed intentionally to ensure that disk 42 fits with different tubes or different tolerances of tubes. In some embodiments, the disk diameter is intentionally substantially the same as the inner diameter of the patient sample tube. This allows a mechanical interaction between the side of the disk and the tube to provide additional support in resisting splashing motion. If the disk is sufficiently sized, the disk and tube can effectively form a soft joint that resists motion of the disk. Thus, the larger waves cannot easily form on the surface of the patient sample fluid. In general, any distance between disk 42 and tube 12 should be substantially smaller than the size of orifice 44. As can be seen, from the pipettes perspective, is unaware of the presence of a disk at all. The only observable difference may be a minor increase in the height of surface 14 due to the displacement of patient fluid by the floating disk. Because level sense mechanisms do not generally rely on such a level of precision, the displacement generally will not affect the operation of pipette 46.

FIG. 5 shows an embodiment where a disk has a non-circular orifice. Disk 50 includes an orifice 52 having a center opening comprising majority of the area of orifice 52 and radial channels 54 which are formed between tabs 56. The center portion of orifice 52 is substantially round (e.g. the tips of the tabs 56 are all approximately the same distance from the center of the disk). The tips of tabs 56 can be concave to create a fully round opening or can be substantially flat/straight creating a polygonal opening that is substantially round (e.g., an octagonal opening where eight tabs are used). The width of channels 54 can vary depending on the application. In some embodiments, the width of channels 54 are substantially wide to form a meniscus with the fluid on which the disk floats. By utilizing channels 54, the overall length of edges making contact with the fluid can be increased and the openings between the channels 54 in the center portion of the orifice can act to break up any waves that begin to form in the orifice 52.

Figure 6:
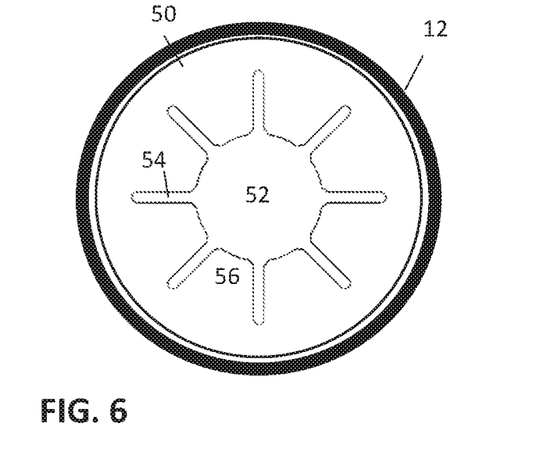
FIG. 6 is a top view of an embodiment of the disk for floating on top of the patient sample fluid, when the disk is placed within a patient sample tube.

FIG. 6 shows disk 50 placed in a tube in a top-down view. In this example, disk 50 floats atop sample fluid with some gap between the edge of the disk and the walls of sample tube 12. This allows the disk to move slightly during motion, allowing the disk to move along with the surface of the fluid. However, the gap between the disk and the tube wall is relatively small, allowing a pipette inserted into the center of tube 12 to always fall within orifice 52, allowing the pipette to interact with the fluid sample without interference by disk 50.

In some embodiments, the disk inserted into the patient sample tube is reusable, and is constructed in such a way that it is washable or autoclavable to fully sanitize the disk for reuse in future patient samples. In some embodiments, the disk is intended to be disposable, being constructed of material suitable for mass production to bring the cost down. Suitable materials for construction of a disk, depending on intended use, can include polypropylene, polystyrene, other rigid polymers, or other materials that may be produced to have a low enough density to float on top the patient sample fluid. In some embodiments, a two-part plastic shell is constructed sealing a gas within the disk, allowing a denser material to be used, but causing the overall density of the disk to be less than that of the patient sample fluid.

In some embodiments, rather than using a floating disk, a plurality of nonconductive floating balls may be placed into the patient sample tube. Because these balls are nonconductive, their presence should not interfere with the level sense mechanism of the pipette. Furthermore, because these balls float independently, they can easily move out of the way of the pipette as it is inserted, without substantially interfering with the aspiration process. These balls may be constructed of any of the materials described with respect to a disk.

Figure 7:
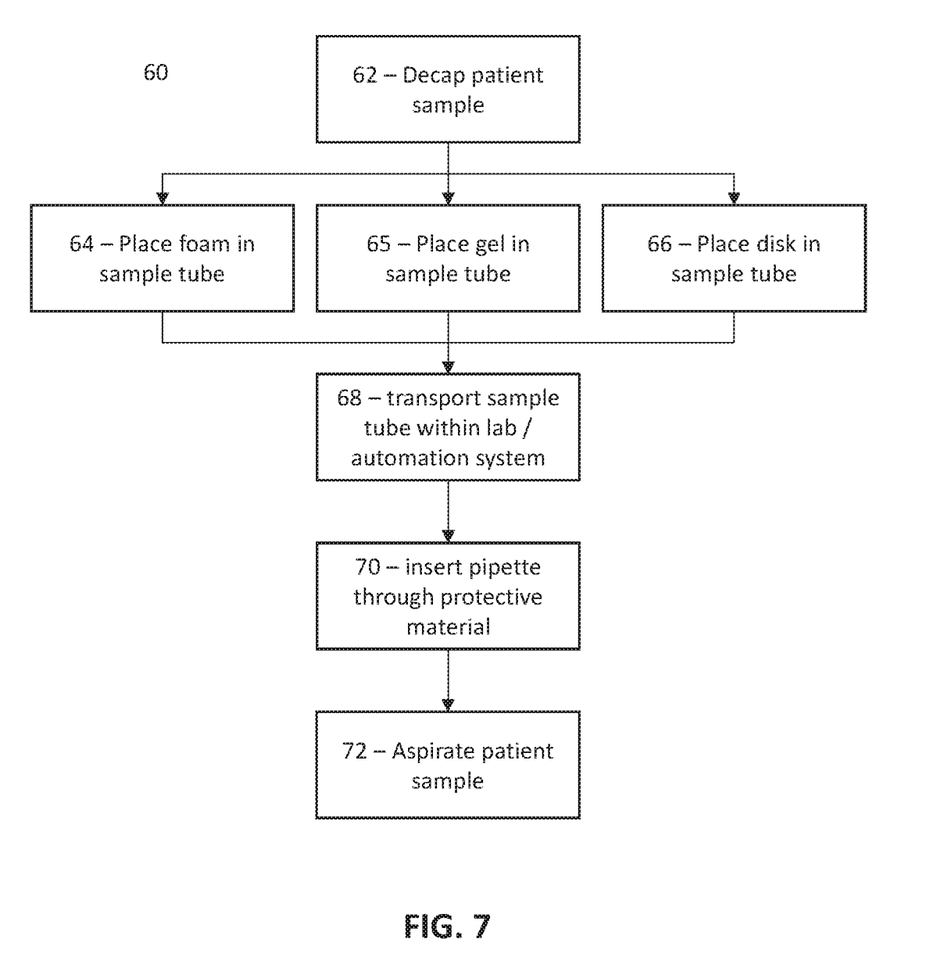
FIG. 7 is a flow chart showing an exemplary method for utilizing a material layer floating atop the patient sample fluid to mitigate splashing motions in the patient sample fluid.

FIG. 7 shows an exemplary method 60 for using any of the materials that are placed atop the patient sample fluid. At step 62 the patient sample tube is de-capped. This can be a manual operation or automatic operation using a mechanical decapper that may be accessible to an automation system in the laboratory environment or as a standalone station. Once the patient sample is de-capped, rapid movement of the sample tube can result in sloshing and splashing. To mitigate this splashing movement, at any of steps 64 through 66, a layer of material is placed atop the patient sample fluid, as explained above.

At step 64 a foam layer may be placed into the sample tube, causing a foam to float atop the patient sample fluid and provide a mechanical mechanism that restricts splashing-type movement (e.g., high-frequency or erratic motion on the surface of the patient sample fluid). Low-speed movement may be less restricted by the foam, as the foam can conform to the surface and changes in the shape of the tube walls with respect to that surface, such as when tilting the tube. However, the density and any a semi-rigidity of the foam can restrict rapid changes to the surface. At step 65, rather than placing a foam layer into the sample tube, a gel is placed into the sample tube, causing the gel to float atop the patient sample fluid and restrict splashing movements as described above. At step 66, rather than a gel or a foam, a disk having an orifice suitable for insertion of a pipette is placed into the sample tube, allowing the disk to float on top of the patient sample fluid. This disk restricts the splashing type movement of the patient sample, while allowing insertion of the pipette.

Once a layer of material is placed atop the patient sample fluid at any of steps 64 through 66, the patient sample is prepared to move through the laboratory environment or automation system with less risk of spillage or splashing. For example, where an automation system is used, the layer of material may be placed onto the patient sample fluid at steps 64 through 66 via a station in the automation system that uses a robot arm to assist in placing the foam, gel, or disk into the sample tube. Then, the automation system, at step 68, transports the sample tube within the automation system to the next station, such as a clinical analyzer attached to the automation system. In embodiments where an automation system may not be used, the layer of material may be used to mitigate splashing of samples in trays that are manually carried throughout the laboratory environment. In such a scenario, step 68 would be carried out manually by an operator of the laboratory equipment.

At step 70, once the patient sample tube has arrived in the destination that interacts with the patient sample, a pipette is inserted into the patient sample fluid. Typically, this pipette is part of a robot arm or mechanical carriage that utilizes actuators to position the pipette substantially near the center (e.g. within 1 to 2 mm) of the vertical axis/center point of the patient sample tube. Then, the pipette is moved via the actuators vertically downward, such that the tip of the pipette is submerged in the patient sample before aspirating the patient sample. By centering and moving of the pipette downward, the pipette moves through the protective material layer on top of the patient sample fluid. The pipette moves through the foam or gel, such that the tip is submerged before aspirating a portion of the patient sample. In foam and gel embodiments, because aspiration does not occur until after the tip is submerged, gel and foam are generally not aspirated along with the fluid. This prevents the foam or gel from contaminating the sample aspirate. In disk embodiments, the disk includes a central orifice that is open where the pipette is inserted. Thus the pipette moves through the protective material layer, without substantial interference from the material. This allows the material to prevent splashing, while also allowing normal aspiration of the patient sample. At step 72, once the pipette tip is submerged in patient sample fluid, a portion of the patient sample fluid is aspirated by the pipette. This is accomplished by producing a negative pressure within the pipette, such as by using a pneumatic mechanism or piston to draw fluid into the pipette.

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

What is claimed is:

1. An assembly used in clinical analysis comprising:
   a patient sample tube having an open mouth at one end;
   patient sample fluid contained within the sample tube; and
   a layer of material floating on a top surface of the patient sample fluid, such that the layer of material floats and restricts splashing movement of the top surface;
   wherein the material is non-porous,
   the material comprises a floating disk having an opening at the center substantially larger than a pipette diameter, and
   the opening includes radial channels.

2. The assembly of claim 1, wherein the material comprises foam.

3. The assembly of claim 1, wherein the material comprises gel.

4. The assembly of claim 1, wherein the opening is substantially circular.

5. A method for mitigating spillage of a patient sample in a laboratory automation system comprising:
   de-capping a patient sample tube comprising a glass tube having an opening and a patient sample fluid contained therein;
   placing a layer of material floating on a top surface of the patient sample fluid such that the layer of material floats and restricts splashing movement of the top surface;
   transporting the patient sample to a pipette station;
   inserting a pipette through the layer of material; and
   aspirating a portion of the patient sample fluid via the pipette,
   wherein the material is non-porous,
   the material comprises a floating disk having an opening at the center substantially larger than a pipette diameter, and
   the opening includes radial channels.

6. The method of claim 5, wherein the material comprises foam.

7. The method of claim 5, wherein the material comprises gel.

8. The method of claim 5, wherein the opening is substantially circular.

9. An apparatus configured to mitigate spillage of patient sample tubes comprising:
   a patient sample tube comprising a cylindrical material having a closed end configured to hold a patient sample fluid and an open end configured to accept a pipette; and
   a round, substantially flat disk configured to be placed within a patient sample tube and to float on the patient sample fluid, comprising a center opening configured to accept the pipette and provide access to the patient sample fluid without exposing the entire surface of the patient sample fluid,
   wherein the opening includes radial channels.

10. The apparatus of claim 9, wherein the center opening is substantially circular.

11. The apparatus of claim 9, wherein the disk is constructed of polypropylene.

12. The apparatus of claim 9, wherein the disk is constructed of polystyrene.

13. The apparatus of claim 9, wherein the disk comprises a hollow structure such that the average density is less than the density of the patient sample fluid.

* * * * *